United States Patent
Kim et al.

(10) Patent No.: US 9,668,821 B2
(45) Date of Patent: Jun. 6, 2017

(54) LAPAROSCOPIC SURGICAL DEVICES HAVING WIRE REDUCER

(71) Applicant: Samsung Electronics Co., Ltd., Suwon-Si, Gyeonggi-Do (KR)

(72) Inventors: Yong Jae Kim, Seoul (KR); Jeong Hun Kim, Hwaseong-si (KR); Kyung Shik Roh, Seongnam-si (KR); Se Gon Roh, Suwon-si (KR); Youn Baek Lee, Suwon-si (KR); Jong Won Lee, Uiwang-si (KR); Byung June Choi, Gunpo-si (KR)

(73) Assignee: Samsung Electronics Co., Ltd., Gyeonngi-Do (KR)

( * ) Notice: Subject to any disclaimer, the term of this patent is extended or adjusted under 35 U.S.C. 154(b) by 393 days.

(21) Appl. No.: 14/188,932

(22) Filed: Feb. 25, 2014

(65) Prior Publication Data
US 2014/0257331 A1 Sep. 11, 2014

(30) Foreign Application Priority Data
Mar. 11, 2013 (KR) .......................... 10-2013-0025636

(51) Int. Cl.
*A61B 19/00* (2006.01)
*A61B 34/30* (2016.01)
(Continued)

(52) U.S. Cl.
CPC .............. *A61B 34/30* (2016.02); *A61B 34/37* (2016.02); *A61B 34/71* (2016.02); *A61B 90/361* (2016.02);
(Continued)

(58) Field of Classification Search
CPC ..... A61B 19/22; A61B 19/00; A61B 19/5212; A61B 19/2203; A61B 2019/2234; A61B 34/30; A61B 34/37; A61B 34/71
See application file for complete search history.

(56) References Cited

U.S. PATENT DOCUMENTS

| 6,394,998 B1 | 5/2002 | Wallace et al. |
| 7,364,582 B2 | 4/2008 | Lee |

(Continued)

FOREIGN PATENT DOCUMENTS

| KR | 20100099818 A | 9/2010 |
| KR | 20110045464 A | 5/2011 |

(Continued)

*Primary Examiner* — Victor Nguyen
(74) *Attorney, Agent, or Firm* — Harness, Dickey & Pierce, P.L.C.

(57) ABSTRACT

Laparoscopic surgical devices include a first member having a first gear, a second member having a second gear corresponding to the first gear, a connection member configured to connect the first member and the second member; first and second wire mounting pieces respectively at the first and second members, a first wire wound on the first wire mounting pieces so as to be pulled upon receiving a first drive force; and a second wire wound on the second wire mounting pieces so as to be pulled upon receiving a second drive force. The drive unit is configured to selectively transmit the first and second amplified driving forces to a respective one the first member and the second member to cause tilting of the first member and the second member.

9 Claims, 14 Drawing Sheets

(51) Int. Cl.
    *A61B 34/00*     (2016.01)
    *A61B 34/37*     (2016.01)
    *A61B 90/00*     (2016.01)

(52) U.S. Cl.
    CPC ... *A61B 2034/305* (2016.02); *A61B 2034/306* (2016.02)

(56) References Cited

U.S. PATENT DOCUMENTS

| | | |
|---|---|---|
| 8,221,450 B2 | 7/2012 | Lee et al. |
| 2009/0143787 A9 | 6/2009 | de la Pena |
| 2009/0171354 A1* | 7/2009 | Deville .............. A61B 18/1445 606/51 |

FOREIGN PATENT DOCUMENTS

| | | |
|---|---|---|
| KR | 20110120476 A | 11/2011 |
| KR | 20110127563 A | 11/2011 |

\* cited by examiner

LAPAROSCOPIC SURGICAL DEVICES HAVING WIRE REDUCER

CROSS-REFERENCE TO RELATED APPLICATION

This application claims the benefit of priority under 35 U.S.C. §119 from Korean Patent Application No. 2013-0025636, filed on Mar. 11, 2013 in the Korean Intellectual Property Office, the disclosure of which is incorporated herein by reference in its entirety.

BACKGROUND

1. Field

Embodiments relate to laparoscopic surgical devices having a wire reducer that may have a reduced size and transmit great drive force.

2. Description of the Related Art

In general, conventional laparotomy for patient treatment is surgical incision through the skin for access to a corresponding site. Laparotomy easily secures field of vision, but causes a great quantity of bleeding during surgery and consequently slow recovery of a patient and large scars due to a large incision site after surgery. Surgery to complement laparotomy is laparoscopic surgery. In laparoscopic surgery, a plurality of small ports is incised in the skin, and an endoscope and various surgical instruments are inserted into the human body through the ports for surgery. Laparoscopic surgery may advantageously leave smaller scars and enable earlier patient recovery after surgery than laparotomy.

In recent years, single-port laparoscopic surgery in which surgical instruments as well as an endoscope are inserted into the human body through a single port present at a specific site, such as the navel, etc., has been attempted. Such single-port surgery is becoming increasingly popular because this may advantageously result in a smaller surgical incision site and a remarkably reduced quantity of bleeding as compared with laparotomy and achieve shortened recovery time and leave only small or no scars.

Such single-port surgery may require a surgical device to move through one port, and therefore the surgical device inserted into the human body may require a great degree of freedom. Conventionally, the surgical device has been configured to be connected to a hard shaft or a bendable tube. Connecting the surgical device to the hard shaft may achieve easy transmission of strong drive force to the surgical device, but may have difficulty in implementing delicate surgical motions. Connecting the surgical device to the bendable tube may increase a degree of freedom with regard to movement of the surgical device, but may not transmit strong drive force to the surgical device. In particular, as the distance between a surgical site and the port incised in the human body increases, transmission of drive force to the surgical devices becomes more difficult.

SUMMARY

Example embodiments provide a laparoscopic surgical device including a wire reducer to achieve an increased degree of freedom in motion during laparoscopic surgery and transmit strong drive force to the surgical device.

In accordance with an example embodiment, a laparoscopic surgical device includes a first member having a first gear at a first side of the first member, a second member having a second gear at a first side of the second member, the second gear corresponding to the first gear, and the second member being connected to the first member to enable tilting of the first member or the second member via movement of the first gear and the second gear engaged with each other. The device further includes a connection member configured to connect the first member and the second member to each other, first wire mounting pieces respectively at the first member and the second member, second wire mounting pieces respectively at the first member and the second member, a first wire wound on the first wire mounting pieces so as to be pulled upon receiving a first amplified drive force from a drive unit, and a second wire wound on the second wire mounting pieces so as to be pulled upon receiving a second amplified drive force from the drive unit, the drive unit being configured to selectively transmit one of the first and second amplified driving forces to a respective one of the first member and the second member to cause tilting of the first member and the second member.

The first amplified drive force transmitted to the first member may be amplified in proportion to a number of turns of the first wire is wound on the first wire mounting, and the second amplified drive force transmitted to the second member may be amplified in proportion to a number of turns of the second wire is wound on the second wire mounting pieces.

If the first wire is pulled by the drive unit, a distance between the first wire mounting pieces may be reduced as compared to before the first wire is pulled and a distance between the second wire mounting pieces is increased as compared to before the first wire is pulled.

The second wire mounting pieces and the first wire mounting pieces may be on opposite sides of the connection member.

A first side of the first wire may be fixed to the first member and a second side of the first wire is fixed to the second member, and a first side of the second wire may be fixed to the first member and a second side of the second wire is fixed to the second member.

A first side of the connection member may be connected to the first member, and a second side of the connection member may be connected to the second member.

If one of the first wire or the second wire is pulled by the drive unit, the first member may be configured to tilt relative to the second member via movement of the first gear and the second gear engaged with each other.

The device further includes a plurality of guides protruding from an outer surface of the first wire mounting piece or an outer surface of the second wire mounting piece.

The first wire or the second wire may be configured to be wound so as to be located between at least one the neighboring guides.

If the first wire is pulled by the drive unit, the first member and the second member may be configured to tilt respectively based on the first and second amplified driving forces applied to the first member and the second member. The first and second amplified driving forces may correspond to N times a number of turns of the first wire and the second wire respectively wound on the first and second wire mounting pieces.

If the first wire is pulled by the drive unit, the second wire may be configured to be selectively pulled toward the first member and the second member by a length equal to a pulled length of the first wire toward the drive unit.

According to another example embodiment, a laparoscopic surgical device includes a first member having a first gear at a first side of the first member, a second member having a second gear at a first side of the second member, an intermediate member having a first connection gear at a first side of the intermediate member and a second connection gear at a second side of the intermediate member, a first wire connected to a drive unit, and a second wire connected to the drive unit. The first connection gear corresponds to the first gear, and the second connection gear corresponds to the second gear. The first member, the second member, and the intermediate member respectively have wire mounting pieces. The first wire is wound plural turns on the wire mounting pieces of the first member and the intermediate member such that a first drive force of the drive unit is amplified and transmitted based on the plural turns of the first wire so as to allow the first member to be tilted relative to the intermediate member via movement of the first gear and the first connection gear engaged with each other. The second wire is wound plural turns on the wire mounting pieces of the intermediate member and the second member such that a second drive force of the drive unit is amplified and transmitted based on the plural turns of the second wire so as to allow the intermediate member to be tilted relative to the second member via movement of the second gear and the second connection gear engaged with each other.

A surface provided with the first connection gear and a surface provided with the second connection gear may be perpendicular to each other.

The first member and the intermediate member may be connected to each other via a first link, and the intermediate member and the second member may be connected to each other via a second link.

The wire mounting pieces may be on opposite sides of the first link or the second link.

The drive unit may be configured to selectively transmit the first and second drive forces to the first member, the intermediate member, and the second member in proportion to the plural turns of the first and second wires wound on the wire mounting pieces.

According to a further example embodiment, a laparoscopic surgical device, includes a first member having a first wire mounting portion and a second wire mounting portion both at a first end of the first member, the first and second wire mounting portions being on opposite sides of the first end of the first member; a second member coupled to the first member, the second member having a third wire mounting portion and a fourth wire mounting portion both at a first end of the second member, the third and fourth wire mounting portions being on opposite sides of the first end of the second member; a first wire wound around the first wire mounting portion and the third wire mounting portion; a second wire wound around the second wire mounting portion and the fourth wire mounting portion; and a drive unit operatively connected to the first wire and the second wire. The drive unit is configured to selectively transmit a drive force to the first member and the second member via the first wire and the second wire. The first and second members are configured to pivot with respect to each other in response to the drive force.

The first member may be coupled to the second member, via a gearing arrangement, to one selected from a pulley, a single shaft, and a link. The link may have a first end connected to the first member and a second end connected to the second member.

The drive unit may be configured to, in a first mode, pull the first wire, and the drive unit may be configured to, in a second mode, pull the second wire.

The drive force may be amplified based on (i) a number of turns the first wire is wound around the first wire mounting portion and the third wire mounting portion and (ii) a number of turns the second wire is wound around the second wire mounting portion and the fourth wire mounting portion.

BRIEF DESCRIPTION OF THE DRAWINGS

Example embodiments will be more clearly understood from the following detailed description taken in conjunction with the accompanying drawings.

FIG. 1 is a view showing a surgical robot according to an example embodiment;

FIG. 2 is a view showing an endoscope surgical unit according to an example embodiment;

FIG. 3 is a partial view of the endoscope surgical unit shown in FIG. 2;

FIG. 4 is a partial view of a laparoscopic surgical device shown in FIG. 3;

FIGS. 5 and 6 are views showing a bent state of the laparoscopic surgical device shown in FIG. 4;

FIG. 7 is an exploded perspective view of the laparoscopic surgical device shown in FIG. 3;

FIG. 8 is a view showing a wire reducer according to an example embodiment;

FIG. 9 is a view showing a joint configuration when the laparoscopic surgical device is bent according to an example embodiment;

FIG. 10 is a view showing a wire mounting piece according to an example embodiment;

FIGS. 11 and 12 are views showing a wire reducer according to another example embodiment; and FIGS. 13 and 14 are views showing a wire reducer according to a further example embodiment.

DETAILED DESCRIPTION

Figure 1:
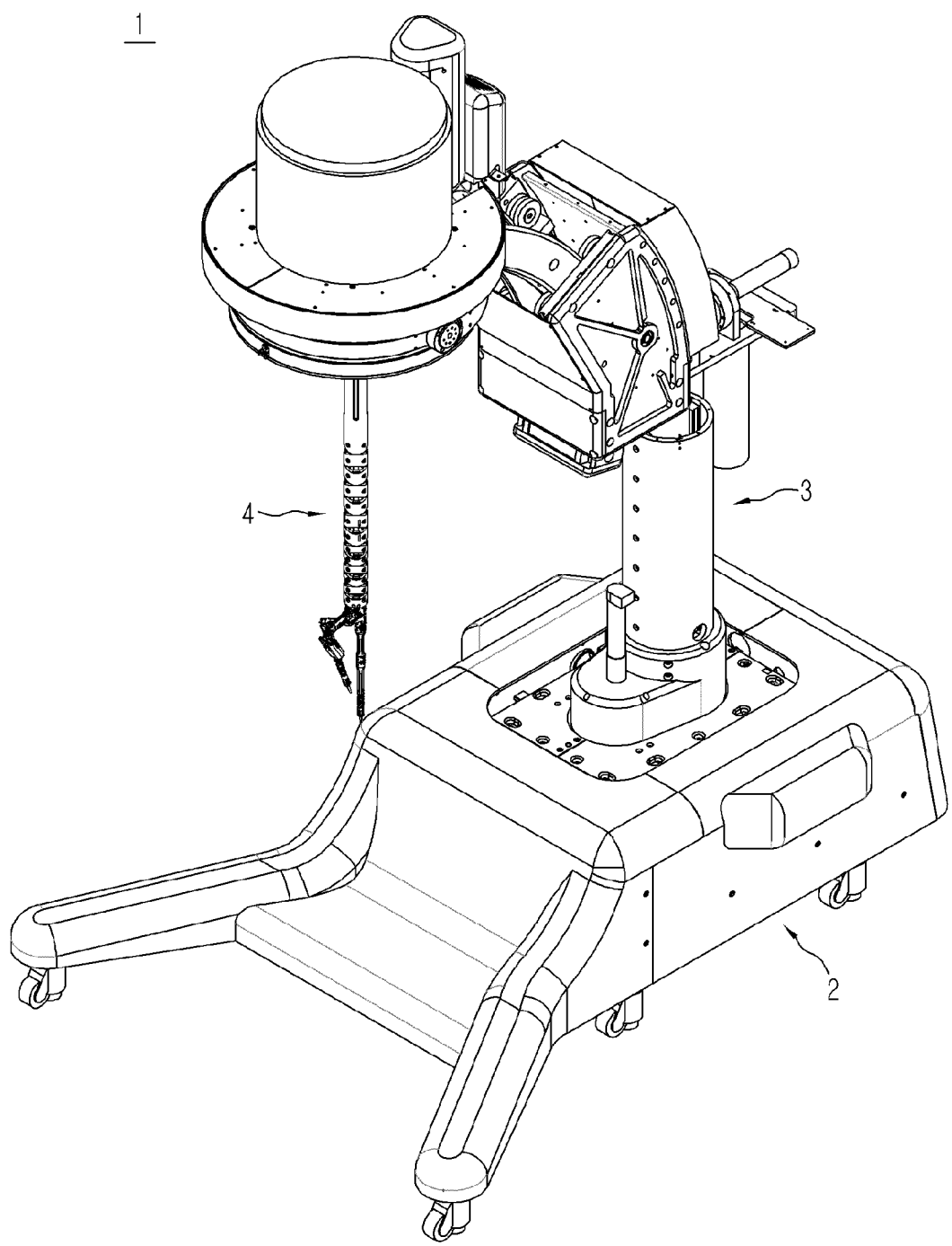
FIGS. 1-14 represent non-limiting, example embodiments as described herein.

Various example embodiments will now be described more fully with reference to the accompanying drawings in which some example embodiments are shown. However, specific structural and functional details disclosed herein are merely representative for purposes of describing example embodiments. Thus, the invention may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments, various features will be described in detail with reference to the attached drawings. However, example embodiments described are not limited thereto.

Hereinafter, a laparoscopic surgical device having a wire reducer according to one embodiment will be described in detail with reference to the accompanying drawings.

Figure 2:
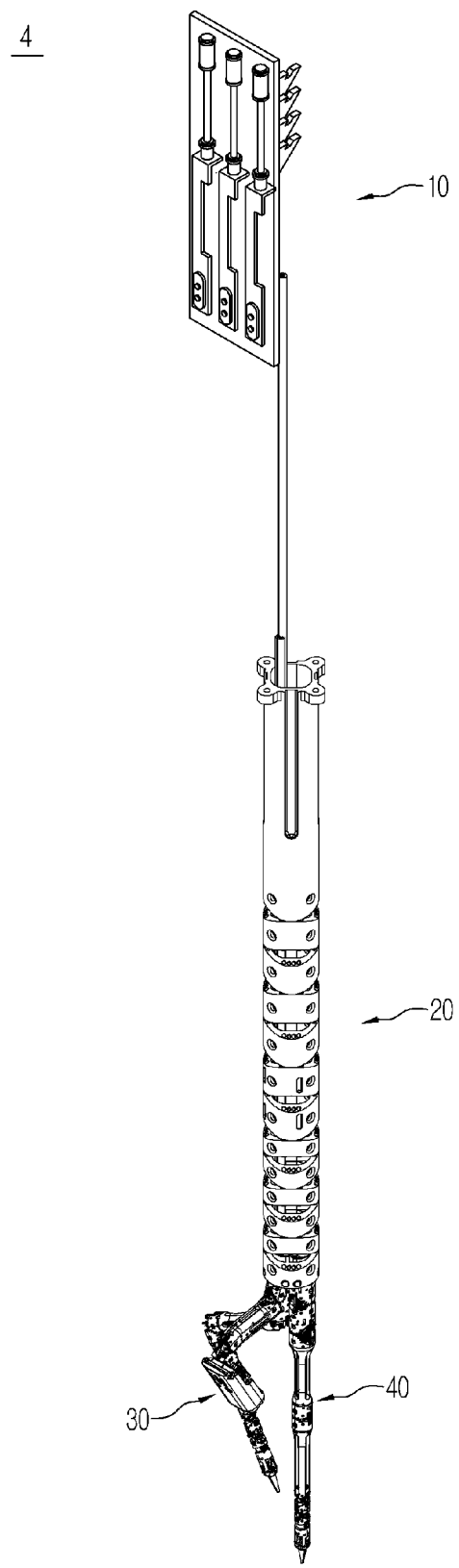

FIG. 1 is a view showing a surgical robot according to an example embodiment, and FIG. 2 is a view showing an endoscope surgical unit according to an example embodiment.

Referring to FIGS. 1 and 2, the surgical robot 1 according to an example embodiment includes a base 2, a support unit 3, and an endoscope surgical unit 4. The base 2 supports the support unit 3, and the endoscope surgical unit 4 is mounted on the support unit 3. The endoscope surgical unit 4 mounted on the support unit 3 is spaced apart from the floor by a set (or, alternatively, predetermined) distance, which may assist an operator in easily performing medical procedures on a patient who lies on an operating table.

The endoscope surgical unit 4 includes a drive unit 10, a connector 20, an endoscope 30, and a laparoscopic surgical device 40. The drive unit 10 may be mounted to the support unit 3. The endoscope 30 may be inserted into the human body to implement medical procedures. The connector 20 connects the endoscope 30, the laparoscopic surgical device 40, and the drive unit 10 to one another. The endoscope 30 and the laparoscopic surgical device 40 may be operated by receiving drive force from the drive unit 10 through the connector 20.

Figure 3:
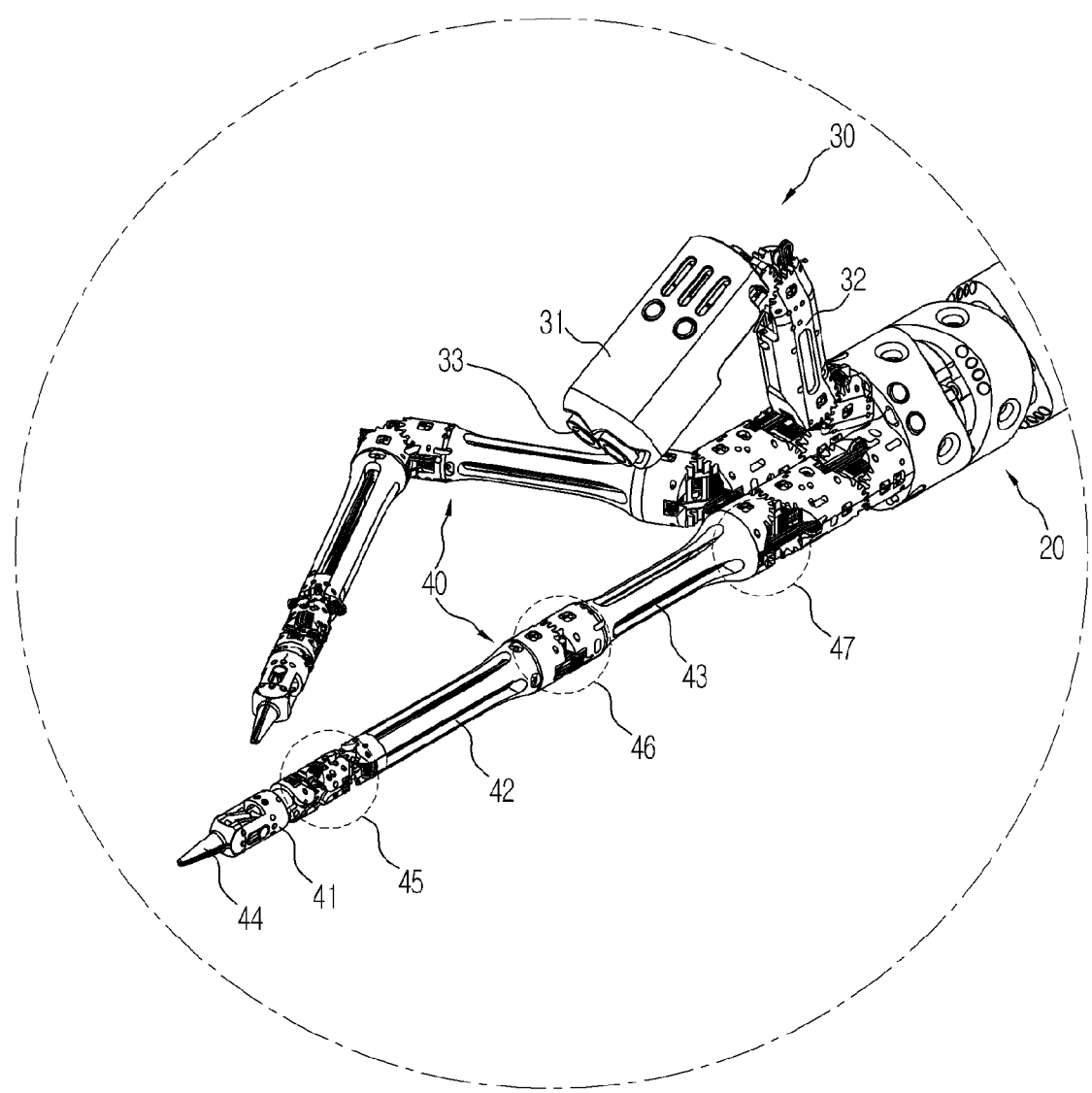

FIG. 3 is a partial view of the endoscope surgical unit shown in FIG. 2.

Referring to FIG. 3, the endoscope surgical unit 4 according to the present example embodiment includes the endoscope 30 and the laparoscopic surgical device 40. The endoscope 30 and the laparoscopic surgical device 40 may be arranged at one end of the connector 20 so as to be inserted into the human body upon surgery. In the present example embodiment, two laparoscopic surgical devices 40 may be provided. The endoscope 30 and the two laparoscopic surgical devices 40 may have a triangular arrangement. In this case, because the endoscope 30 may watch and capture an image of the two laparoscopic surgical devices 40, the endoscope 30 easily secures field of vision for imagining of motions of the laparoscopic surgical devices 40 and thus may easily capture images of a surgical site and motions of the laparoscopic surgical devices 40 from various angles.

The endoscope 30 includes a head 31 and an arm 32. The head 31 may be connected to the arm 32, and in turn the arm 32 may be connected to the connector 20. A camera 33 may be provided at one side of the head 31. A joint may be interposed between the head 31 and the arm 32 to enable tilting of the head 31. A joint may also be provided between the arm 32 and the connector 20 to enable tilting of the arm 32. In addition, a joint may be provided in the head 31 to enable leftward or rightward rotation of the head 31. As the above-described joints allow the head 31 to bend to various angles, the camera 33 provided at one side of the head 31 may capture images of a surgical site as well as motions of the laparoscopic surgical devices 40 at various positions.

The laparoscopic surgical device 40 may include a plurality of joints. The laparoscopic surgical device 40 may bend about the joints so as to easily perform surgical motions. For example, the laparoscopic surgical device 40 may include a first arm 41, a second arm 42 and a third arm 43, a first joint 45 may be interposed between the first arm 41 and the second arm 42, and a second joint 46 may be interposed between the second arm 42 and the third arm 43. The first arm 41 may be tilted about the first joint 45 and the second arm 42 may be tilted about the second joint 46. The third arm 43 may be connected to the connector 20 so as to be tilted by the third joint 47. A surgical instrument 44, to perform surgery, may be mounted at an end of the first arm 41.

Figure 4:
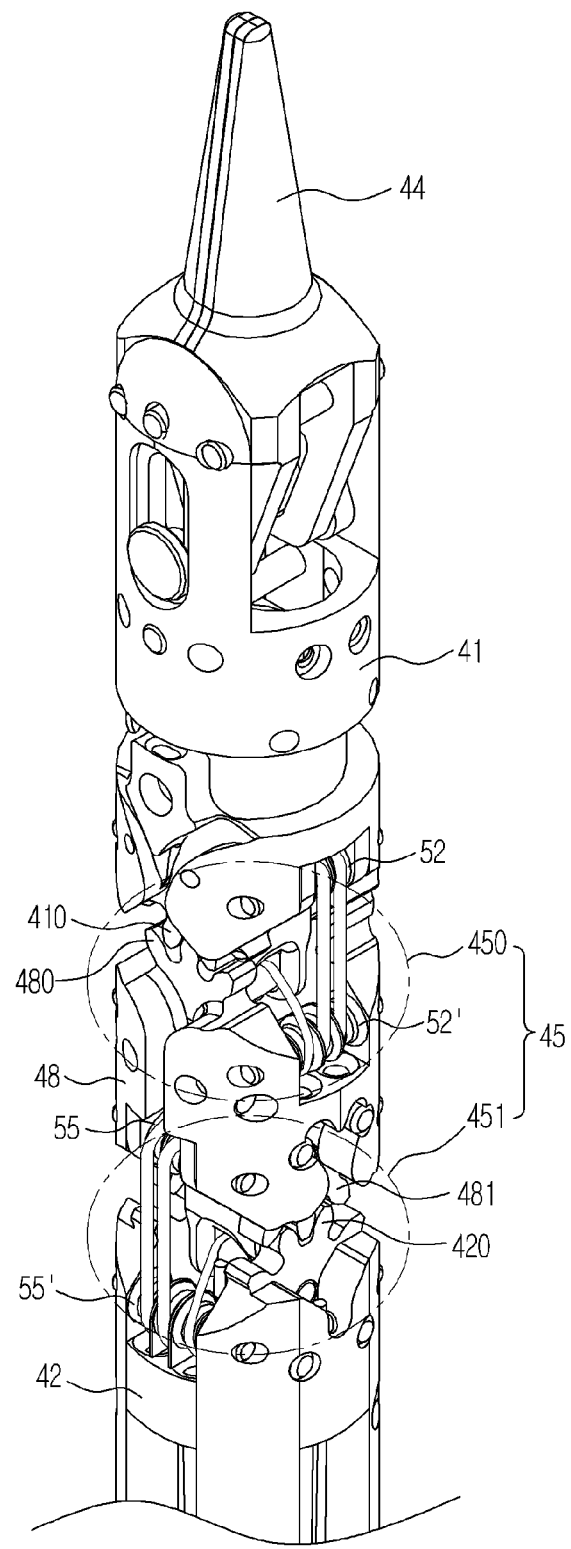
Figure 5:
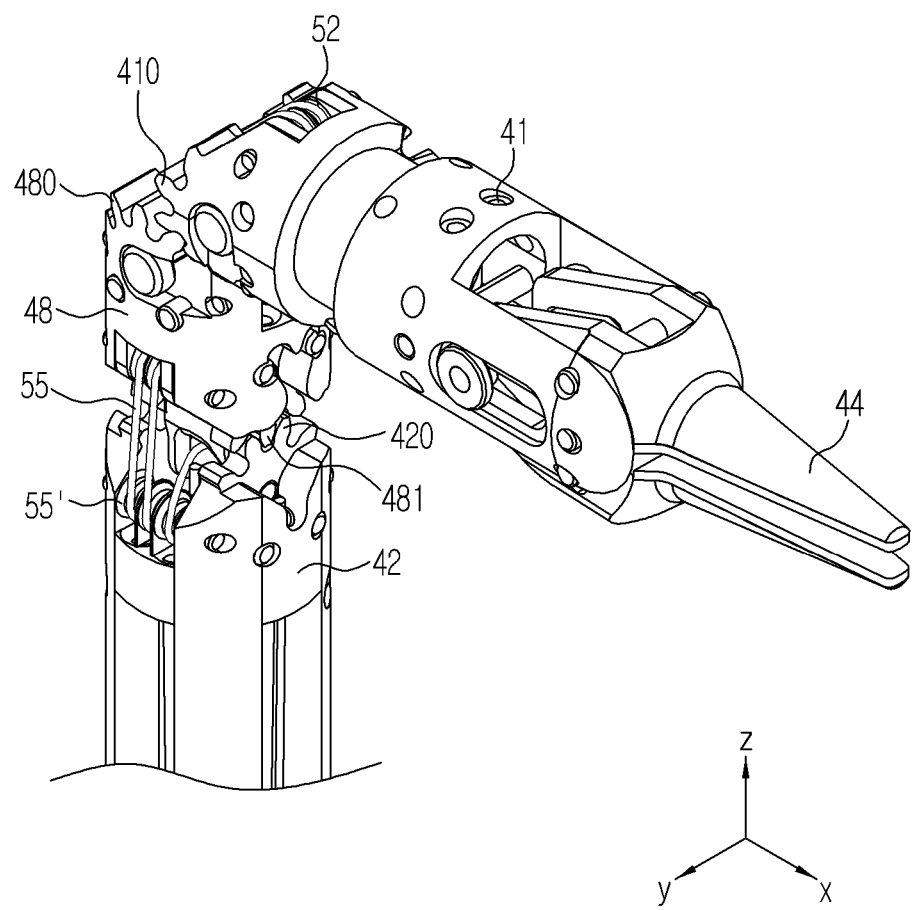
Figure 6:
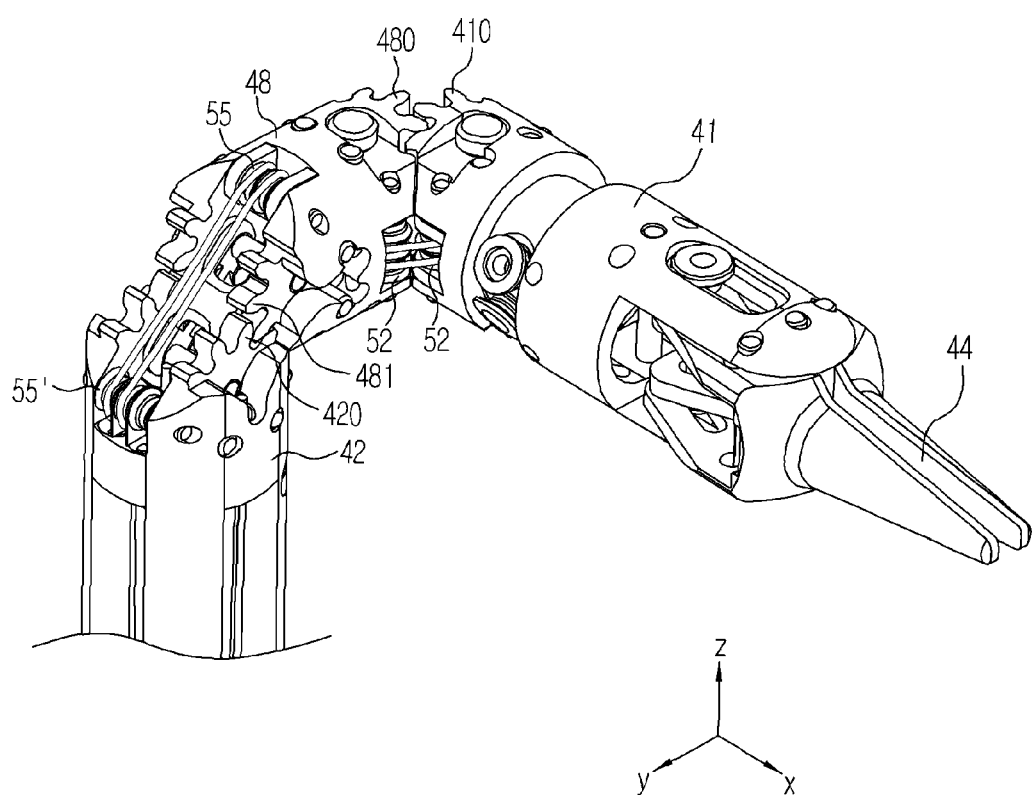

FIG. 4 is a partial view of the laparoscopic surgical device shown in FIG. 3, and FIGS. 5 and 6 are views showing a bent state of the laparoscopic surgical device shown in FIG. 4.

Referring to FIGS. 4 to 6, the plurality of arms included in the laparoscopic surgical device 40 according to the present example embodiment may respectively have at least 2 degrees of freedom provided by the joints between the neighboring arms.

For example, the first joint 45 includes a first motion joint 450 and a second motion joint 451. The first arm 41 may be tilted about the first motion joint 450. In addition, the first arm 41 may be tilted about the second motion joint 451. In this case, a tilting direction of the first arm 41 by the first motion joint 450 and a tilting direction of the first arm 41 by the second motion joint 451 may be perpendicular to each other.

For example, the first arm 41, as exemplarily shown in FIGS. 5 and 6, may be rotated and tilted about the y-axis by the first motion joint 450 and may be rotated and tilted about the x-axis by the second motion joint 451.

The first motion joint 450 and the second motion joint 451 may take the form of rolling joints to be rotatably engaged with gears of the adjacent arms. A wire connected to the drive unit 10 may be wound on the gears such that the gears are rotated upon receiving drive force transmitted through the wire.

Hereinafter, a configuration of the first joint included in the laparoscopic surgical device according to one embodiment will be described. The plurality of joints including the second joint, the third joint, etc. may have a configuration and operation similar to those of the first joint.

Figure 7:
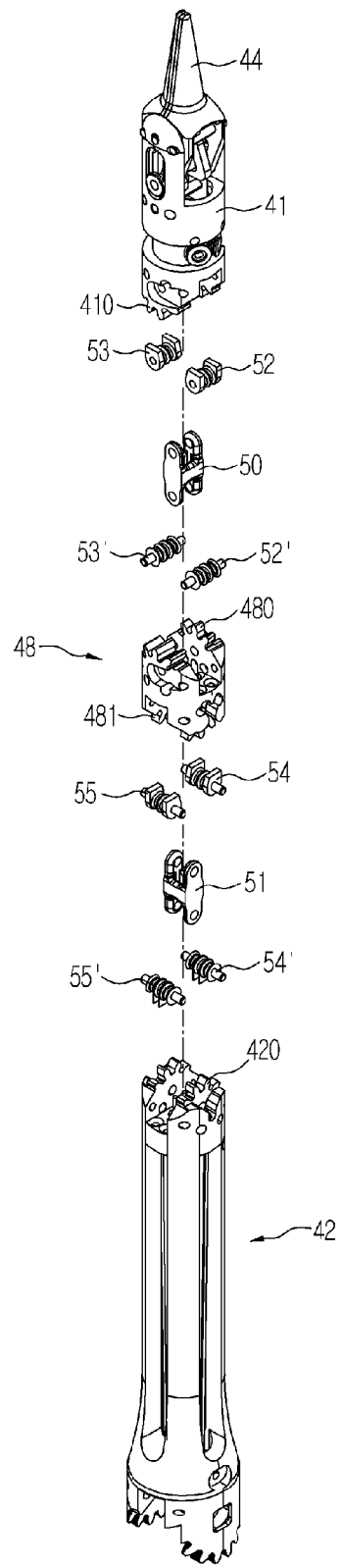

FIG. 7 is an exploded perspective view of the laparoscopic surgical device shown in FIG. 3.

Referring to FIGS. 4 and 7, the first joint 45 of the laparoscopic surgical device 40 according to the present example embodiment includes the first motion joint 450 and the second motion joint 451. As described above, the first arm 41 may be rotated and tilted about the y-axis by the first motion joint 450 and may be rotated and tilted about the x-axis by the second motion joint 451.

An intermediate member 48 may be provided between the first arm 41 and the second arm 42. A first connection gear 480 may be formed at one side of the intermediate member 48 and a second connection gear 481 may be formed at the other side of the intermediate member 48. The first connection gear 480 and the second connection gear 481 may constitute a gearing arrangement. The first connection gear 480 and the second connection gear 481 may extend perpendicular to each other. For example, the first connection gear 480 may extend along the x-axis, and the second connection gear 481 may extend along the y-axis. The first arm 41 may be connected to the first connection gear 480 and the second arm 42 may be connected to the second connection gear 481.

The surgical instrument 44 may be mounted at one side of the first arm 41 and a first gear 410 may be formed at the other side of the first arm 41. The first gear 410 may correspond to the first connection gear 480 formed at the intermediate member 48. The first gear 410 and the first connection gear 480 are engaged and rotated together, causing tilting of the first arm 41.

The first arm 41 and the intermediate member 48 may be connected to each other via a first link 50. One side of the first link 50 may be mounted to the first arm 41 and the other side of the first link 50 may be mounted to the intermediate member 48. Thereby, the first arm 41 may be tilted in a state in which the first arm 41 and the intermediate member 48 are connected to each other. The first link 50 may serve as a connection member that connects the first arm 41 and the intermediate member 48 to each other.

The first arm 41 and the intermediate member 48 may be provided with wire mounting pieces 52, 52', 53, and 53'. The wire mounting pieces 52, 52', 53, and 53' may include first wire mounting pieces 52 and 52' and second wire mounting pieces 53 and 53'. The wire mounting pieces 52, 52', 53 and 53' may extend in a direction perpendicular to an extension direction of the first gear 410 and the first connection gear 480.

The first wire mounting pieces 52 and 52' and the second wire mounting pieces 53 and 53' may be located respectively at front and rear positions in a movement direction of the first gear 410 when the first arm 41 is tilted. More specifically, the second wire mounting pieces 53 and 53' may be located to opposite to the first wire mounting pieces 52 and 52' about the first link 50. For example, assuming that a position of the first link 50 is a zero point of coordinates, if the first arm 41 is rotated and tilted about the y-axis, the first gear 410 may be moved along the x-axis, and the first wire mounting pieces 52 and 52' and the second wire mounting pieces 53 and 53' may be located on the +x-axis and on the −x-axis respectively.

A first wire 61 (shown in FIG. 8) connected to the drive unit 10 may be wound plural turns on the first wire mounting pieces 52 and 52'. A second wire 60 (shown in FIG. 8) connected to the drive unit 10 may be wound plural turns on the second wire mounting pieces 53 and 53'. If any one of the first wire 61 or the second wire 60 is pulled by the drive unit 10, the first arm 41 may be rotated and tilted toward the pulled wire. As the first wire 61 and the second wire 62 are wound plural turns on the wire mounting pieces, these wires may serve as a reducer. This will be described later.

The first motion joint 450 includes the first gear 410 formed at the first arm 41, the first link 50, and the first connection gear 480 of the intermediate member 48. As described above, the first arm 41 may be tilted by the first motion joint 450.

The second motion joint 451 includes the second connection gear 481 formed at the intermediate member 48, a second link 51, and the second gear 420 formed at one side of the second arm 42. The first arm 41 may be tilted by the second motion joint 451. As described above, the tilting direction of the first arm 41 by the first motion joint 450 may be perpendicular to the tilting direction of the first arm 41 by the second motion joint 451.

A configuration of the second motion joint 451 may be similar to that of the first motion joint 450, although the first and second motion joints 450 and 451 cause different tilting directions of the first arm 41. The second connection gear 481 may be provided at the other side of the intermediate member 48, and the second gear 420 corresponding to the second connection gear 481 may be provided at one side of the second arm 42. As described above, the second connection gear 481 may be provided at a surface perpendicular to a surface where the first connection gear 480 is formed.

The intermediate member 48 and the second arm 42 may be connected to each other via the second link 51. The second connection gear 481 may be formed at the other side of the intermediate member 48 and the second gear 420 may be formed at one side of the second arm 42. In a state in which the intermediate member 48 and the second arm 42 are connected to each other via the second link 51, the second connection gear 481 and the second gear 420 may be engaged and rotated with each other. Through rotation of the second connection gear 481 and the second gear 420 engaged with each other, the intermediate member 48 and the first arm 41 connected to the intermediate member 48 may be tilted. The second link 51 may serve as a connection member to connect the intermediate member 48 and the second arm 42 to each other.

Wire mounting pieces 54, 54', 55 and 55' may be provided at the intermediate member 48 and the second arm 42. The wire mounting pieces 54, 54', 55, and 55' include third wire mounting pieces 54 and 54' and fourth wire mounting pieces 55 and 55'. The third wire mounting pieces 54 and 54' and the fourth wire mounting pieces 55 and 55' may extend in a direction perpendicular to an extension direction of the second connection gear 481 and the second gear 420.

The third wire mounting pieces 54 and 54' and the fourth wire mounting pieces 55 and 55' may be respectively at front and rear positions in a movement direction of the second connection gear 481 when the first arm 41 is tilted. More specifically, the fourth wire mounting pieces 55 and 55' may be located opposite to the third wire mounting pieces 54 and 54' about the second link 51. For example, assuming that a position of the second link 51 is a zero point of coordinates, if the intermediate member 48 and the first arm 41 are rotated and tilted about the x-axis, the second connection gear 481 may be moved along the y-axis, and the third wire mounting pieces 54 and 54' and the fourth wire mounting pieces 55 and 55' may be located on the +y-axis and on the −y-axis respectively.

A third wire (not shown) connected to the drive unit 10 may be wound plural turns on the third wire mounting pieces 54 and 54'. A fourth wire (not shown) connected to the drive unit 10 may be wound plural turns on the fourth wire mounting pieces 55 and 55'. If any one of the third wire or the fourth wire is pulled by the drive unit 10, the first arm 41 and the intermediate member 48 may be rotated and tilted toward the pulled wire. As the third wire and the fourth wire are wound plural turns on the wire mounting pieces, these wires may serve as a reducer.

Hereinafter, tilting accomplished by the wires and reducer functions of the wires will be described.

Figure 8:
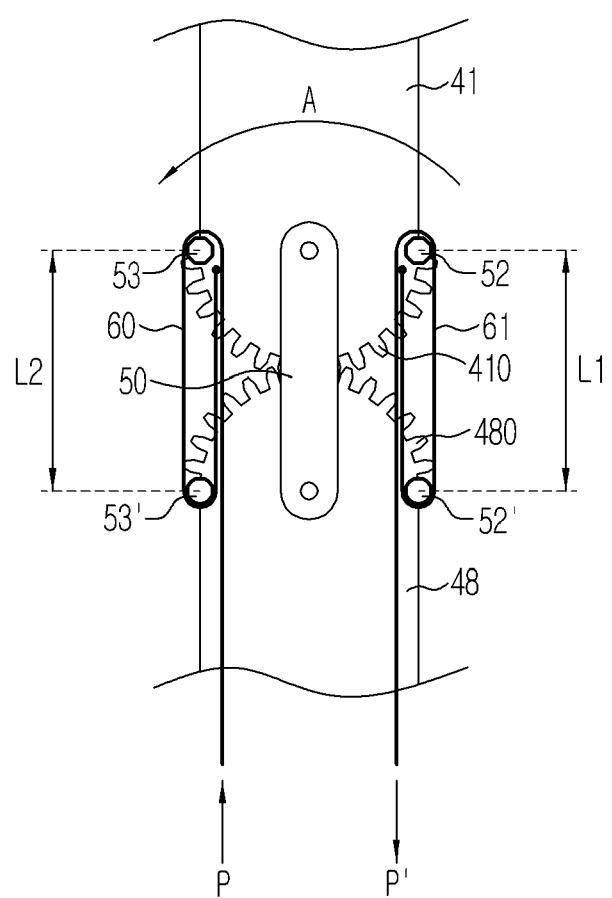
Figure 9:
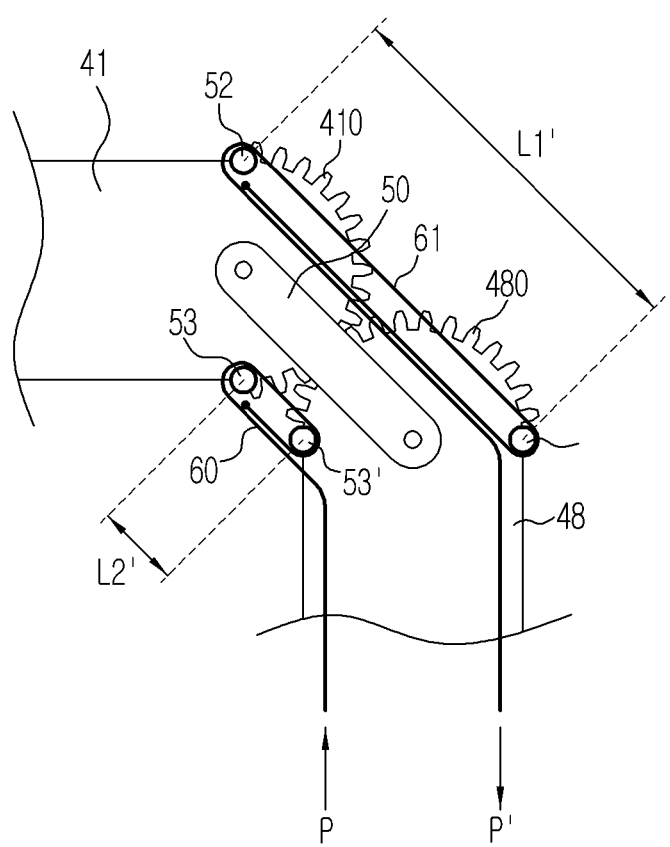

FIG. 8 is a view showing a wire reducer according to an example embodiment, and FIG. 9 is a view showing a joint configuration when the laparoscopic surgical device is bent according to an example embodiment.

Referring to FIGS. 8 and 9, the first arm 41 according to the present example embodiment may be tilted by force applied to the first wire 61 or the second wire 60. The first wire 61 and the second wire 60 may be connected to the drive unit 10, and the drive unit 10 may pull any one of the first wire 61 or the second wire 62. The first wire 61 and the second wire 60 may be fixed to the first gear 410. For example, the wire mounting pieces 52 and 53 provided at the sides of the first arm 41 with the first gear 410 or at the first gear 410 have holes for passage of the wires 60 and 61. After the wires 61 and 60 pass through the holes, ends of the wires may be knotted or may be provided with interference members such that the ends of the wires have a greater diameter than that of the holes. As such, the wires 60 and 61 may be fixed to the first gear 410.

The first gear 410 of the first arm 41 may be engaged with the first connection gear 480 to thereby be rotated in a pulling direction of the wire. Thereby, tilting of the first arm 41 is implemented. In this case, a distance between the wire mounting pieces located toward the pulled wire is reduced, and a distance between the wire mounting pieces toward the wire that is not pulled is increased.

For example, if the drive unit 10 pulls the second wire 60 in a direction P, the first gear 410 engaged with the first connection gear 480 is rotated in a direction A. In this case, a distance L2' between the second wire mounting pieces 53 and 53' after rotation is less than a distance L2 between the second wire mounting pieces 53 and 53' before rotation. A distance L1' between the first wire mounting pieces 52 and 52' after rotation is greater than a distance L1 between the first wire mounting pieces 52 and 52' before rotation. When not considering friction, etc., a reduced length (L2-L2') of the second wire 60 wound on the second wire mounting pieces 53 and 53' after rotation may be equal to an extended length (L1'-L1) of the first wire 61 wound on the first wire mounting pieces 52 and 52' after rotation. In addition, when not considering friction, etc., force of pulling the second wire 60 in a direction P may be equal to force applied to the first wire 61 in a direction P'.

As the first wire 61 is wound plural turns on the first wire mounting pieces 52 and 52', the drive unit 10 may amplify drive force applied to the first wire 61, thereby transmitting the amplified drive force to the first gear 410. Similarly, as the second wire 60 is wound plural turns on the second wire mounting pieces 53 and 53', the drive unit 10 may amplify drive force applied to the second wire 60, thereby transmitting the amplified drive force to the first gear 410. As such, rigidity of the wires 60 and 61 may increase in proportion to the square of N.

In one example, in the case in which the first wire 61 is wound N turns on the first wire mounting pieces 52 and 52', if the drive unit 10 pulls the first wire 61 by force of 1 kgf, the first wire 61 pulls the first wire mounting pieces 52 and 52' by force of N kgf. As a result, as force of the drive unit 10 is amplified N times to pull the wire mounting pieces 52 and 52', the first gear 410 is rotated. In this case, if the first wire 61 is moved by a distance of T m, a distance between the first wire mounting pieces 52 and 52' before and after rotation may vary by a difference of T/N m. That is, a moved distance of the first wire 61 by the drive unit 10 is N times a distance difference between the first wire mounting pieces 52 and 52'. Here, the number of turns N of the first wire 61 refers to the number of reciprocal movements of the first wire 61 on the first wire mounting pieces 52 and 52'.

Although the above description focuses on the first wire 61, this may be similarly applied to the second wire 60, the third wire 62, and the fourth wire 63. If the wire is wound N turns on the wire mounting pieces, this may mean that the wire has a reduction ratio of N:1. To reduce friction between the wire and the wire mounting pieces, the wire may be provided, via the gearing arrangement, with a pulley.

Referring to FIGS. 8 and 9, it will be appreciated that the first wire 61 is wound three turns on the first wire mounting pieces 52 and 52'. Accordingly, if the drive unit 10 applies force of 1 kgf to the first wire 61 in a direction P, force of 3 kgf may be applied between the first wire mounting pieces 52 and 52'. If the first wire 61 is moved 1 m toward the drive unit 10, a distance between the first wire mounting pieces 52 and 52' may be reduced by ⅓ m. Thereby, the first gear 410 is moved and rotated along the first connection gear 480, and the first arm 41 is tilted. In this case, it will be appreciated that the first motion joint 450 has a reduction ratio of 3:1.

The above-described configuration in which a wire is wound N turns between two members to amplify the magnitude of input force may be referred to as a wire reducer. With the above-described wire reducer configuration, although there is no gain in terms of work by the drive unit 10, drive force applied to the joint is amplified N times, rigidity of the wire is increased in proportion to the square of N, and a moved distance of the wire toward the drive unit 10 is reduced to 1/N, which may advantageously achieve accurate and delicate motions of the laparoscopic surgical device during surgery.

The wire reducer condition may be applied to various robots having joints as well as the laparoscopic surgical device. Although the configuration in which the intermediate member is provided between the first arm and the second arm to realize two degrees of freedom has been described above, the wire reducer configuration may be applied to a joint configuration in which the first arm and the second arm are directly connected to each other to realize one degree of freedom.

Figure 10:
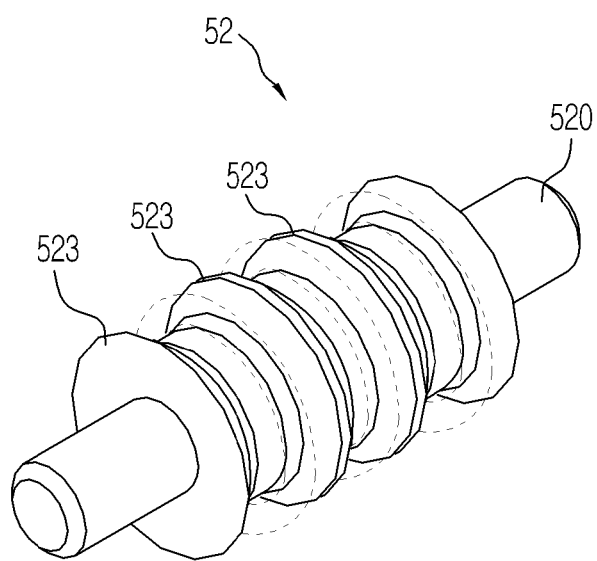

FIG. 10 is a view showing the wire mounting piece according to an example embodiment.

Referring to FIG. 10, the wire mounting piece according to the present example embodiment may be provided with a plurality of protruding guides to ensure stable wire winding. In one example, a plurality of ring-shaped guides 523 may be formed at the exterior of a mounting portion 520 of the first wire mounting piece 52. As the first wire 61 is wound between the neighboring guides 523, the first wire 61 may be stably mounted and moved even if the drive unit 10 applies force to the first wire 61 mounted on the first wire mounting piece 52.

Figure 11:
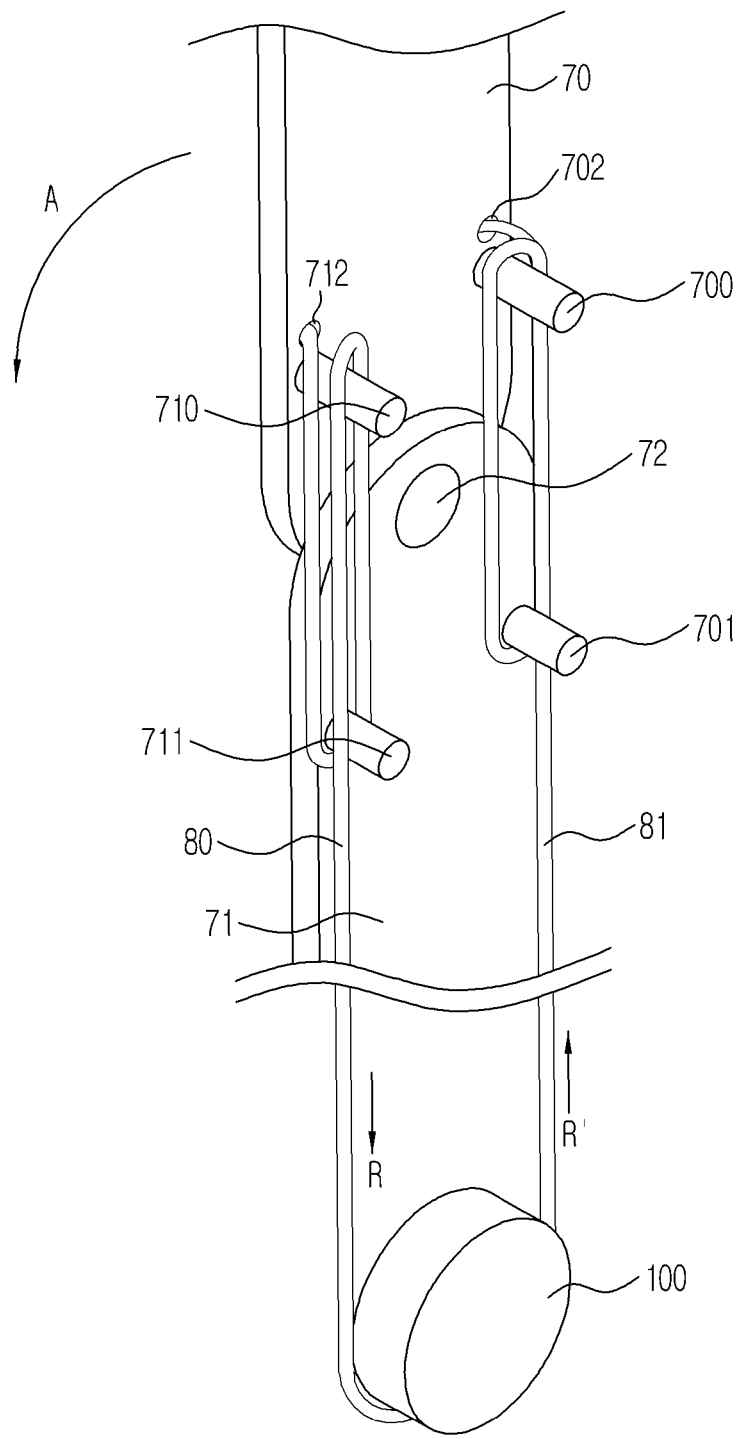
Figure 12:
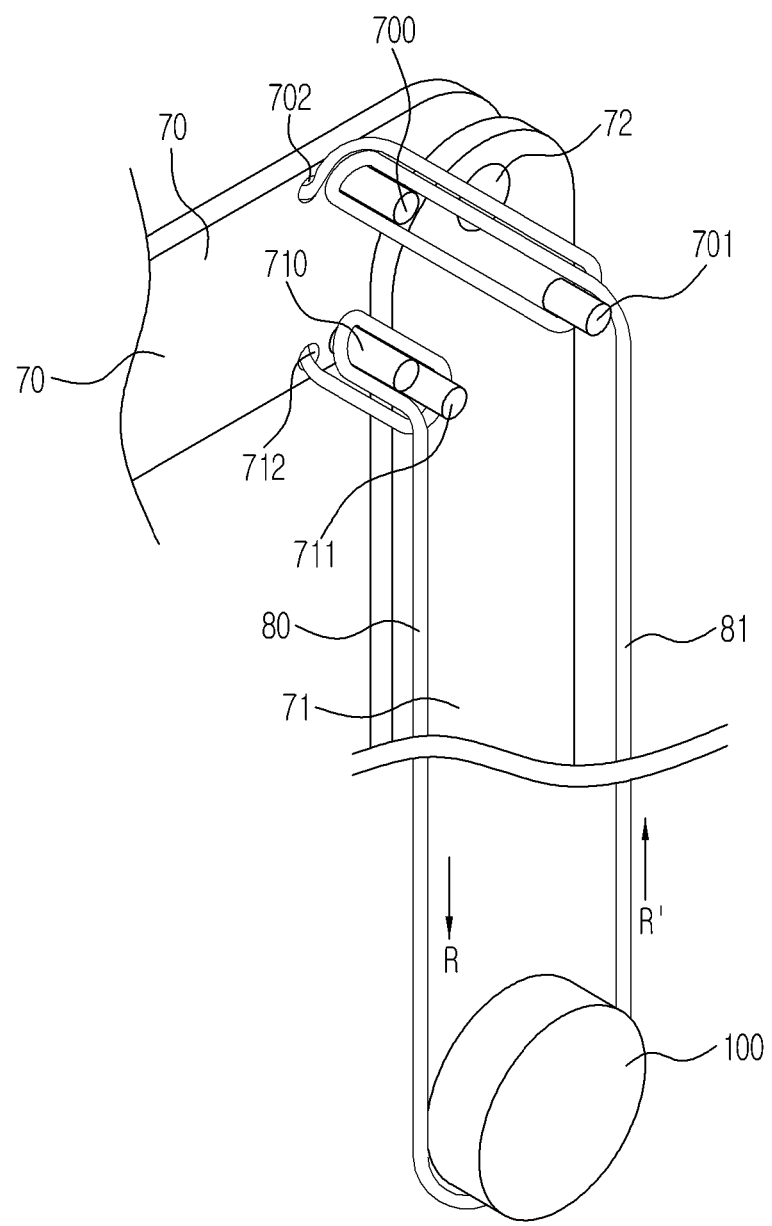

FIGS. 11 and 12 are views showing a wire reducer according to another example embodiment.

Referring to FIG. 11, the joint according to the present example embodiment may be configured in such a manner that a first member 70 and a second member 71 are directly coupled to a rotation center 72. The first member 70 and the second member 71 may have holes respectively, and may be connected to each other via a shaft penetrating the holes. In this case, the shaft serves as the rotation center 72. The shaft provided at the rotation center 72 may also referred to as a connection member that connects the first member 70 and the second member 71 to each other.

The first member 70 may be rotated and tilted about the rotation center 72. As described above, the wire reducer configuration may be applied even to a configuration in which the first member 70 and the second member 71 are directly coupled to each other about the rotation center 72.

The first member 70 and the second member 71 may be provided at one side thereof with first wire mounting pieces 700 and 701, and at the other side thereof with second wire mounting pieces 710 and 711. A first wire 81 connected to a drive unit 100 may be wound N turns on the first mounting pieces 700 and 701, and a second wire 80 connected to the drive unit 100 may be wound N turns on the second wire mounting pieces 710 and 711.

Similar to the joint according to the example embodiment described above, any one of the first wire 81 or the second wire 80 may be pulled by the drive unit 100. The first member 70 may be rotated toward the pulled wire.

In one example, as exemplarily shown in FIGS. 11 and 12, the second wire 80 may be wound three turns on the second wire mounting pieces 710 and 711. If the drive unit 100 pulls the second wire 80 in a direction R, the first member 70 may be rotated in a direction A. In this case, a distance between the second wire mounting pieces 710 and 711 on which the second wire 80 is wound is reduced, and a distance between the first wire mounting pieces 700 and 701 is increased. If the drive unit 100 applies force of 1 kgf, force of 3 kgf may be applied to the second wire mounting pieces 710 and 711. If the second wire 80 is moved 1 m by the drive unit 100, a distance between the second wire mounting pieces 710 and 711 may be reduced by ⅓ m.

Figure 13:
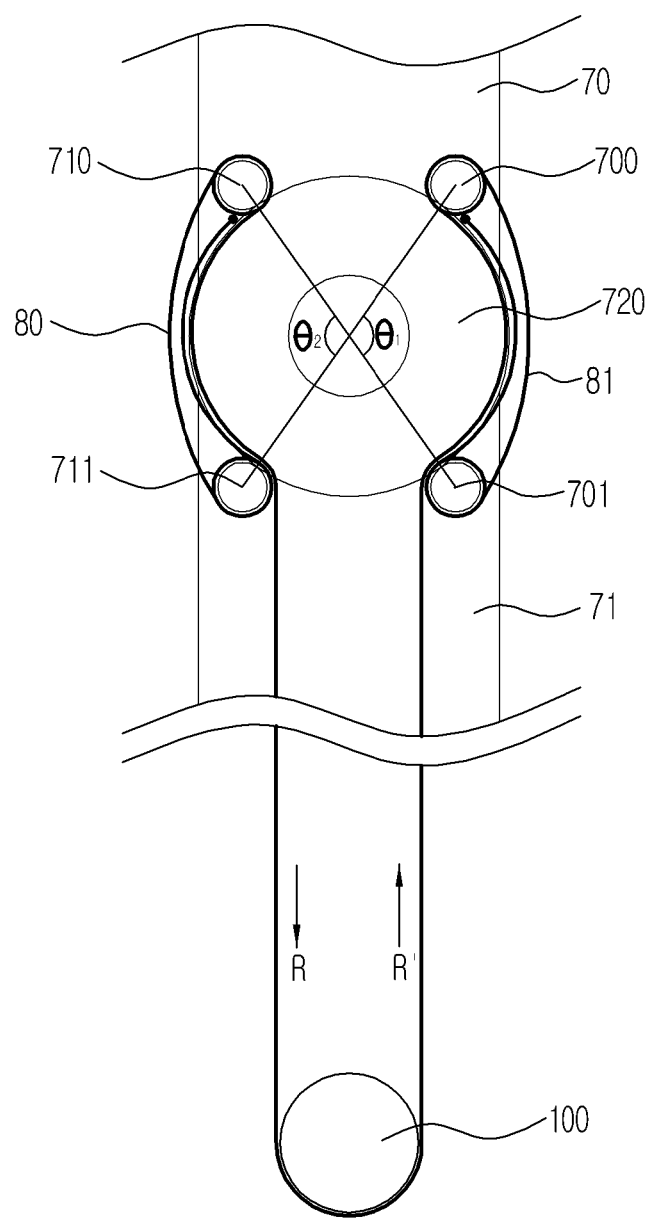
Figure 14:
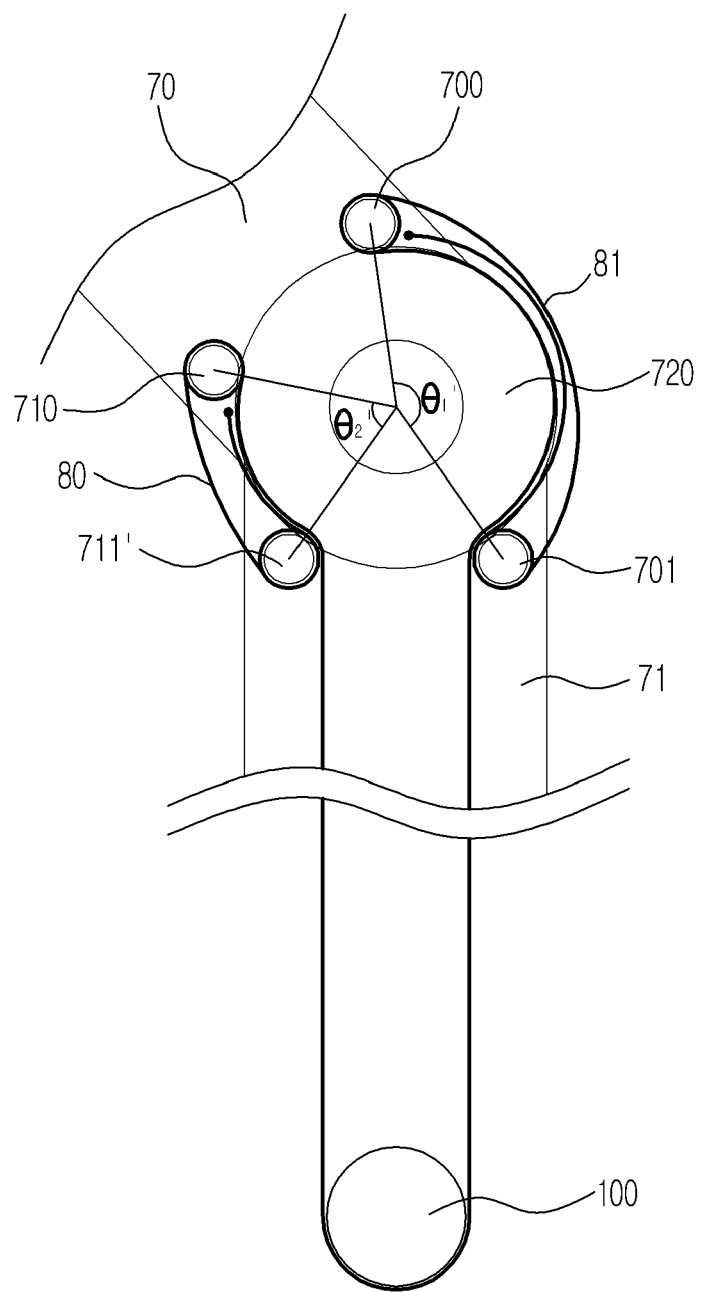

FIGS. 13 and 14 are views showing a wire reducer according to a further example embodiment.

Referring to FIGS. 13 and 14, the joint according to the present example embodiment may be provided at a rotation center thereof with a pulley 720. Similar to the joint according to the above-described example embodiment, the first member 70 and the second member 71 may be directly connected to each other at the rotation center, and the first member 70 or the second member 71 may be rotatable about the rotation center.

The first wire mounting pieces 700 and 701 may be mounted respectively at one side of the first member 70 and at one side of the second member 71, and the first wire 81 connected to the drive unit 100 may be wound N turns on the first wire mounting pieces 700 and 701. The second wire mounting pieces 710 and 711 may be mounted respectively at the other side of the first member 70 and at the other side of the second member 71, and the second wire 80 connected to the drive unit 100 may be wound N turns on the second wire mounting pieces 710 and 711.

The pulley 720 is mounted at the rotation center. A distance between the wire mounting pieces 700 and 710 provided at the first member 70 and a distance between the wire mounting pieces 710 and 711 provided at the second member 71 are less than a diameter of the pulley 720. As such, the wire wound on the wire mounting piece, as exemplarily shown in FIG. 13, may come into contact with a partial outer surface of the pulley 720. As the wire comes into contact with the outer surface of the pulley 720, it may be possible to reduce friction between the wire mounting pieces and the wire when the wire is pulled by the drive unit. This may prevent the wire from passing the rotation center caused when the tilting member is rotated by a large angle, which may ensure stable implementation of tilting.

In a state in which the first member 70 and the second member 71 are arranged in a straight line, the center angle of an arc, along which the first wire 81 comes into contact with the outer surface of the pulley 720, may be designated by $\theta_1$, and the center angle of an arc, along which the second wire 80 comes into contact with the outer surface of the pulley 720, may be designated by $\theta_2$. In this case, $\theta_1$ and $\theta_2$ may be equal to each other.

If the drive unit 100 applies force to the second wire 80 in a direction R, a distance between the second wire mounting pieces 710 and 711 is reduced, and the first member 70 is rotated in a direction A. Thereby, the first member 70 may be tilted. The first wire 81 and the second wire 80 may be moved along the outer surface of the pulley 720. Assuming that the center angle of an arc, along which the first wire 81 comes into contact with the outer surface of the pulley 720 after rotation, is $\theta_1'$, $\theta_1'$ is greater than $\theta_1$ before rotation. In addition, assuming that the center angle of an arc, along which the second wire 80 comes into contact with the outer surface of the pulley 720 after rotation, is $\theta_2'$, $\theta_2'$ is greater than $\theta_2$ before rotation.

Even in this case, force of the drive unit 100 may be amplified in proportion to the number of turns of the wire on the wire mounting pieces. The length of the wire between the wire mounting pieces may be reduced by 1/N the moved distance of the wire by the drive unit 100.

That is, as exemplarily shown in FIGS. 13 and 14, in a state in which the wire is wound three turns on the wire mounting pieces, if the drive unit 100 pulls the second wire 80 in a direction R by applying force of 1 kgf, force of 3 kgf may be applied to the second wire mounting pieces 710 and 711. If the second wire 80 is moved 1 m in the direction R, the length of the second wire 80 wound on the second wire mounting pieces 710 and 711 may be reduced by ⅓ m.

The above-described wire reducer configuration may be applied to various surgical robots, home robots, industrial robots, etc., in addition to the laparoscopic surgical device. The wire reducer configuration according to the example embodiments may advantageously provide a device having great degrees of freedom with great drive force. In addition, because the drive unit is located at the outside of the device and only the reducer is provided at the device, reduction in the size of the device may be accomplished. In particular, with regard to the laparoscopic surgical device that needs delicate and accurate motions as well as a reduced size, the wire reducer configuration according to the example embodiments may accomplish several advantages including great drive force, enhanced rigidity, and implementation of delicate motions.

As is apparent from the above description, according to one example embodiment, a laparoscopic surgical device may be delicately operated in various directions to realize delicate motions upon laparoscopic surgery. In addition, accurate surgery may be accomplished via transmission of strong drive force to the surgical device.

Although the example embodiments have been shown and described, it would be appreciated by those skilled in the art that changes may be made in the embodiment without departing from the principles and spirit of the invention, the scope of which is defined in the claims and their equivalents.

What is claimed is:

1. A laparoscopic surgical device, the device comprising:
a first member having a first gear at a first side of the first member;
a second member having a second gear at a first side of the second member,
the second gear corresponding to the first gear, and
the second member being connected to the first member to enable tilting of the first member or the second member via movement of the first gear and the second gear engaged with each other;
a connection member configured to connect the first member and the second member to each other;
first wire mounting pieces respectively at the first member and the second member;
second wire mounting pieces respectively at the first member and the second member;
a first wire wound on the first wire mounting pieces so as to be pulled upon receiving a first amplified drive force from a drive unit; and
a second wire wound on the second wire mounting pieces so as to be pulled upon receiving a second amplified drive force from the drive unit,
the drive unit being configured to selectively transmit one of the first and second amplified driving forces to a respective one of the first member and the second member to cause tilting of the first member and the second member, wherein
if the first wire is pulled by the drive unit, the first member and the second member are configured to tilt respectively based on the first and second amplified driving forces applied to the first member and the second member, and
the first and second amplified driving forces correspond to N times a number of turns of the first wire and the second wire respectively wound on the first and second wire mounting pieces.

2. The device according to claim 1, wherein if the first wire is pulled by the drive unit, a distance between the first wire mounting pieces is reduced as compared to before the first wire is pulled and a distance between the second wire mounting pieces is increased as compared to before the first wire is pulled.

3. The device according to claim 1, wherein the second wire mounting pieces and the first wire mounting pieces are on opposite sides of the connection member.

4. The device according to claim 1, wherein
a first side of the first wire is fixed to the first member and a second side of the first wire is fixed to the second member, and
a first side of the second wire is fixed to the first member and a second side of the second wire is fixed to the second member.

5. The device according to claim 1, wherein
a first side of the connection member is connected to the first member, and
a second side of the connection member is connected to the second member.

6. The device according to claim 5, wherein if one of the first wire or the second wire is pulled by the drive unit, the first member is configured to tilt relative to the second member via movement of the first gear and the second gear engaged with each other.

7. The device according to claim 1, further comprising:
a plurality of guides protruding from an outer surface of the first wire mounting piece or an outer surface of the second wire mounting piece.

8. The device according to claim 7, wherein the first wire or the second wire is configured to be wound so as to be located between at least one the neighboring guides.

9. The device according to claim 1, wherein if the first wire is pulled by the drive unit, the second wire is configured to be selectively pulled toward the first member and the second member by a length equal to a pulled length of the first wire toward the drive unit.

* * * * *